(12) United States Patent
Reyes et al.

(10) Patent No.: US 8,668,330 B2
(45) Date of Patent: Mar. 11, 2014

(54) EYEWEAR WITH LENS RETENTION MECHANISM

(75) Inventors: Carlos Reyes, Rancho Santa Margarita, CA (US); Ryan Anthony Calilung, Irvine, CA (US); Jason Paul Janavicius, Laguna Niguel, CA (US); Hanz Karsten Moritz, Foothill Ranch, CA (US)

(73) Assignee: Oakley, Inc., Foothill Ranch, CA (US)

( * ) Notice: Subject to any disclaimer, the term of this patent is extended or adjusted under 35 U.S.C. 154(b) by 255 days.

(21) Appl. No.: 13/209,039

(22) Filed: Aug. 12, 2011

(65) Prior Publication Data

US 2012/0038879 A1    Feb. 16, 2012

Related U.S. Application Data

(60) Provisional application No. 61/373,698, filed on Aug. 13, 2010.

(51) Int. Cl.
*G02C 1/04* (2006.01)
(52) U.S. Cl.
USPC .......................................... 351/106; 351/110
(58) Field of Classification Search
USPC .......... 351/86, 83, 103, 106, 41, 92, 90, 105, 351/110
See application file for complete search history.

(56) References Cited

U.S. PATENT DOCUMENTS

| | | |
|---|---|---|
| 1,308,477 A | 7/1919 | Blanchard |
| 1,588,775 A | 6/1926 | Schumacher |
| 2,391,361 A | 12/1945 | Stevenson |
| 2,443,422 A | 6/1948 | Hansen |
| 2,504,157 A | 4/1950 | Rosenheim |
| 2,652,746 A | 12/1950 | Shanks |
| 3,214,767 A | 11/1965 | Weber |
| 3,229,303 A | 1/1966 | Jonassen |
| 3,383,707 A | 5/1968 | McNeill |
| 3,395,964 A | 8/1968 | Chartrice |
| 3,552,840 A | 1/1971 | Braget |

(Continued)

FOREIGN PATENT DOCUMENTS

| | | |
|---|---|---|
| EP | 0121018 | 10/1984 |
| EP | 0496292 | 1/1991 |

(Continued)

OTHER PUBLICATIONS

International Search Report and Written Opinion in International Application No. PCT/US2011/047676, dated Nov. 17, 2011 in 11 pages.

*Primary Examiner* — Hung Dang
(74) *Attorney, Agent, or Firm* — Knobbe Martens Olson & Bear, LLP

(57) ABSTRACT

Eyewear is provided that can comprise a frame, a lens, and at least one lens retention mechanism that can secure the lens relative to the frame. The frame can support at least one lens in a field of view of a wearer. The frame can include a first ear stem and a second ear stem that allows the frame to be worn on the wearer's head. The retention mechanism can be supported by the frame and/or the lens and can be movable or fixed relative to the frame and/or the lens. In some embodiments, the retention mechanism comprises a latch device having an engagement structure that moves along a path of motion that intersects the lens. The retention component can engage an engagement portion of the lens to securing the lens relative to the frame.

21 Claims, 10 Drawing Sheets

(56) References Cited

U.S. PATENT DOCUMENTS

| | | |
|---|---|---|
| 3,826,564 A | 7/1974 | Werling, Sr. |
| 3,829,201 A | 8/1974 | Whiting |
| 3,931,646 A | 1/1976 | Loughner |
| 4,056,853 A | 11/1977 | Bottazzini et al. |
| 4,176,921 A | 12/1979 | Matthias |
| 4,264,987 A | 5/1981 | Runckel |
| 4,304,469 A | 12/1981 | Solomon |
| 4,340,282 A | 7/1982 | Murakami |
| 4,357,080 A | 11/1982 | Solomon |
| 4,515,448 A | 5/1985 | Tackles |
| 4,527,291 A | 7/1985 | Nussbickl |
| 4,616,367 A | 10/1986 | Jean et al. |
| 4,686,712 A | 8/1987 | Spiva |
| 4,715,702 A | 12/1987 | Dillon |
| 4,813,775 A | 3/1989 | Kaksonen |
| 4,822,158 A | 4/1989 | Porsche |
| 4,843,655 A | 7/1989 | Hegendorfer |
| 4,859,048 A | 8/1989 | Jannard |
| 4,867,550 A | 9/1989 | Jannard |
| 4,901,374 A | 2/1990 | Van der Woude |
| 4,951,322 A | 8/1990 | Lin |
| 5,048,944 A | 9/1991 | Porsche |
| 5,056,163 A | 10/1991 | Chou |
| 5,144,344 A | 9/1992 | Takahashi et al. |
| 5,182,587 A | 1/1993 | Hyoi |
| 5,208,614 A | 5/1993 | Jannard |
| 5,270,743 A | 12/1993 | Hofmair et al. |
| 5,357,292 A | 10/1994 | Wiedner |
| 5,373,331 A | 12/1994 | Vallalla et al. |
| 5,390,369 A | 2/1995 | Tubin |
| 5,400,089 A | 3/1995 | Danloup et al. |
| 5,418,580 A | 5/1995 | Sondrol |
| 5,467,148 A | 11/1995 | Conway |
| 5,536,828 A | 7/1996 | Deluca et al. |
| 5,541,674 A | 7/1996 | Jannard |
| 5,576,775 A | 11/1996 | Bolle |
| 5,583,583 A | 12/1996 | Wilson |
| 5,587,747 A | 12/1996 | Bernheiser |
| 5,602,603 A | 2/1997 | Bondet |
| 5,610,668 A | 3/1997 | Mage |
| 5,617,588 A | 4/1997 | Canavan et al. |
| 5,638,145 A | 6/1997 | Jannard et al. |
| 5,648,832 A | 7/1997 | Houston et al. |
| 5,652,954 A | 8/1997 | Paiement et al. |
| 5,689,323 A | 11/1997 | Houston et al. |
| 5,708,489 A | 1/1998 | Jannard |
| 5,752,280 A | 5/1998 | Hill |
| 5,760,866 A | 6/1998 | Wedeck et al. |
| 5,768,716 A | 6/1998 | Porsche |
| 5,802,622 A | 9/1998 | Baharad et al. |
| 5,805,261 A | 9/1998 | Houston et al. |
| 5,815,235 A | 9/1998 | Runckel |
| 5,862,529 A | 1/1999 | Moodie et al. |
| 5,898,469 A | 4/1999 | Wang |
| 5,914,767 A | 6/1999 | Wedeck et al. |
| 5,929,963 A | 7/1999 | McNeal |
| 5,963,293 A | 10/1999 | Jannard |
| 5,969,789 A | 10/1999 | Houston et al. |
| 5,971,536 A | 10/1999 | Chiu |
| 5,987,702 A | 11/1999 | Simioni |
| 6,007,199 A | 12/1999 | Yang |
| 6,009,564 A | 1/2000 | Tackles et al. |
| 6,010,217 A | 1/2000 | Houston et al. |
| 6,010,218 A | 1/2000 | Houston et al. |
| 6,086,199 A | 7/2000 | Holland et al. |
| 6,106,116 A | 8/2000 | Houston et al. |
| 6,168,271 B1 | 1/2001 | Houston et al. |
| 6,193,367 B1 | 2/2001 | Lee |
| 6,224,209 B1 | 5/2001 | Chen |
| 6,250,756 B1 | 6/2001 | Jannard |
| 6,273,564 B1 | 8/2001 | Wedeck et al. |
| 6,282,727 B1 | 9/2001 | Lindahl |
| 6,296,357 B1 | 10/2001 | Bof |
| 6,349,422 B1 | 2/2002 | Schleger et al. |
| 6,357,873 B1 | 3/2002 | Spindelbalker |
| 6,428,165 B1 | 8/2002 | Rivera |
| 6,533,412 B1 | 3/2003 | Wang et al. |
| 6,550,912 B2 | 4/2003 | Vitaloni |
| 6,561,647 B1 | 5/2003 | Chen |
| 6,637,877 B1 | 10/2003 | Hartley et al. |
| 6,712,465 B1 | 3/2004 | Teng |
| 6,742,890 B1 | 6/2004 | Teng |
| 6,742,891 B2 | 6/2004 | Chen |
| 6,786,592 B2 | 9/2004 | Rivera |
| 6,863,395 B1 | 3/2005 | Teng |
| 6,923,537 B2 | 8/2005 | Hartley et al. |
| 6,926,404 B2 | 8/2005 | Bassahon et al. |
| 6,929,364 B1 | 8/2005 | Jannard |
| 6,948,813 B2 | 9/2005 | Parks |
| 6,959,988 B1 | 11/2005 | Sheldon |
| 6,964,067 B1 | 11/2005 | Hartman |
| 6,964,477 B1 | 11/2005 | Teng |
| 7,000,263 B2 | 2/2006 | McNeal |
| 7,003,802 B2 | 2/2006 | Broersma |
| 7,058,991 B2 | 6/2006 | Hartman et al. |
| 7,090,346 B2 | 8/2006 | Tsai |
| 7,100,215 B2 | 9/2006 | Shiue |
| 7,137,700 B2 | 11/2006 | DiChiara et al. |
| 7,163,289 B2 | 1/2007 | Wedeck et al. |
| 7,200,875 B2 | 4/2007 | Dondero |
| 7,219,992 B1 | 5/2007 | Wu |
| 7,219,993 B1 | 5/2007 | Chiou |
| 7,222,958 B1 | 5/2007 | Chiou |
| 7,222,959 B2 | 5/2007 | Jannard |
| 7,234,808 B2 | 6/2007 | Bruck |
| 7,241,007 B2 | 7/2007 | Cody |
| 7,343,631 B2 | 3/2008 | Lin |
| 7,452,069 B2 | 11/2008 | Lipawsky |
| 7,481,529 B1 | 1/2009 | Chen |
| 7,497,569 B2 | 3/2009 | Webb |
| 7,520,605 B1 | 4/2009 | Chen |
| 7,553,013 B2 | 6/2009 | Tsai |
| 7,681,257 B1 | 3/2010 | Broersma |
| 7,686,449 B2 | 3/2010 | Jannard et al. |
| 7,712,894 B2 | 5/2010 | Tsai |
| 7,712,896 B1 | 5/2010 | Lee |
| 7,725,959 B2 | 6/2010 | Wang-Lee |
| 7,810,174 B2 | 10/2010 | Matera |
| 7,850,301 B2 | 12/2010 | DiChiara |
| 7,856,673 B2 | 12/2010 | Reed |
| 7,887,181 B1 | 2/2011 | Chen |
| D639,845 S | 6/2011 | Fuchs |
| D640,725 S | 6/2011 | Moritz et al. |
| 7,954,942 B2 | 6/2011 | Calilung et al. |
| 8,192,015 B2 | 6/2012 | Taylor et al. |
| 8,316,470 B2 | 11/2012 | McNeal et al. |
| 8,408,695 B2 | 4/2013 | Calilung et al. |
| 8,414,119 B2 | 4/2013 | Yeh |
| 8,534,830 B2 | 9/2013 | Taylor et al. |
| 2004/0141147 A1 | 7/2004 | Cyr |
| 2005/0132478 A1 | 6/2005 | Canavan |
| 2005/0270477 A1 | 12/2005 | Curci et al. |
| 2006/0048289 A1 | 3/2006 | Shiue |
| 2006/0119790 A1 | 6/2006 | Tsai |
| 2006/0179554 A1 | 8/2006 | Barton |
| 2006/0191062 A1 | 8/2006 | Matera |
| 2006/0250571 A1 | 11/2006 | Li |
| 2006/0256281 A1 | 11/2006 | Li |
| 2007/0024806 A1 | 2/2007 | Blanshay et al. |
| 2007/0033718 A1 | 2/2007 | Lin |
| 2007/0109490 A1 | 5/2007 | Collier et al. |
| 2007/0121059 A1 | 5/2007 | Chiou |
| 2007/0153230 A1 | 7/2007 | Musal et al. |
| 2008/0137028 A1 | 6/2008 | Webb |
| 2008/0155736 A1 | 7/2008 | Paulson et al. |
| 2008/0198323 A1 | 8/2008 | Siu |
| 2008/0301858 A1 | 12/2008 | Wang-Lee |
| 2008/0304005 A1 | 12/2008 | DiChiara |

(56) References Cited

U.S. PATENT DOCUMENTS

| | | |
|---|---|---|
| 2009/0019620 A1 | 1/2009 | Reed |
| 2009/0038059 A1 | 2/2009 | McNeal et al. |
| 2009/0300830 A1 | 12/2009 | Mage |
| 2009/0313746 A1 | 12/2009 | Wang |
| 2010/0085533 A1 | 4/2010 | Calilung et al. |
| 2011/0007262 A1 | 1/2011 | Taylor et al. |
| 2011/0194065 A1 | 8/2011 | Belbey et al. |
| 2011/0225709 A1 | 9/2011 | Saylor et al. |
| 2011/0225710 A1 | 9/2011 | Reyes et al. |
| 2011/0225711 A1 | 9/2011 | Reyes et al. |
| 2011/0299026 A1 | 12/2011 | Calilung et al. |
| 2012/0038879 A1 | 2/2012 | Reyes et al. |
| 2012/0218507 A1 | 8/2012 | Calilung et al. |
| 2012/0255104 A1 | 10/2012 | Didier |
| 2013/0083285 A1 | 4/2013 | McNeal et al. |
| 2013/0104300 A1 | 5/2013 | Park |

FOREIGN PATENT DOCUMENTS

| | | | |
|---|---|---|---|
| EP | 1810648 | | 7/2007 |
| EP | 1830221 | | 9/2007 |
| FR | 1126329 | | 11/1956 |
| FR | 2088866 | | 1/1972 |
| FR | 2626683 | | 8/1989 |
| FR | 2688322 | | 12/1992 |
| FR | 2684292 | | 6/1993 |
| FR | 2 800 173 | | 4/2001 |
| GB | 512419 | | 9/1939 |
| GB | 2199155 | | 6/1988 |
| GB | 2278459 | | 11/1994 |
| JP | 219021 | | 2/1990 |
| WO | WO 98/30930 | | 7/1998 |
| WO | WO 03/023495 | | 3/2003 |
| WO | WO 2010/003143 | * | 1/2010 |
| WO | WO 2010/081043 | | 7/2010 |

* cited by examiner

EYEWEAR WITH LENS RETENTION MECHANISM

CROSS-REFERENCE TO RELATED APPLICATIONS

This application claims the benefit of U.S. Provisional Application No. 61/373,698, filed Aug. 13, 2010, the entirety of which is incorporated herein by reference.

BACKGROUND

1. Field of the Inventions

The present inventions relate generally to mounting systems for eyewear, and more specifically to methods and apparatuses for mounting and retaining optical lenses.

2. Description of the Related Art

A wide variety of improvements have been made in recent years in the eyewear field, particularly with respect to eyewear intended for use in active sports or as fashion sunglasses. These eyewear designs provide a variety of functional improvements, such as maximizing interception of peripheral light, reducing optical distortion and increasing the wearer's comfort level, compared to previous active sport eyewear.

A continuing objective in the field of high quality eyewear, particularly that is intended for use in high speed action sports, is minimizing distortion introduced by the eyewear. Distortion may be introduced by any of a variety of influences, such as poor construction materials for the optical portion of the lens and inferior polishing and/or molding techniques for the lens. In addition, optical distortion can result from the interaction of the lens with the frame, such as changes in the shape of the lens orbital or poor orientation of the lens with respect to the wearer's normal line of sight.

Eyeglass systems which use a polymeric or metal wire frame are especially susceptible to bending and flexing due to a variety of environmental causes such as impact, storage-induced forces, forces resulting from the assembly process of the eyewear, and exposure to sunlight and heat. Flexing of the lens or uncontrolled deviation of the orientation of one lens with respect to the other or with respect to the ear stems can undesirably change the optical characteristics of the eyeglasses, whether the optical lens is corrective (prescription) or noncorrective.

Additionally, many eyewear systems are assembled in which the lens is retained using an interference fit. Dual lens eyewear comprises a frame having a pair of orbitals that support lenses of the eyeglasses. The frame is usually formed as a single component that is later hingedly attached to left and right ear stems that allow the eyeglasses to be worn by a user. In some cases, the left and right orbitals generally continuously surround the respective left and right lenses. In order to accommodate the lenses in the orbitals of the frame, the orbitals may include a groove that runs within the perimeter of the orbital. The bottom of the groove is generally formed to match the perimeter geometry of the lens. During assembly of the eyeglass, the lens is forcibly inserted into the groove of the orbital to produce a very tight interference fit. Unfortunately, that deformation can produce optical distortions or other unwanted stresses on the lenses.

A further consideration in eyeglass design is the ease of interchangeability of the lens. In dual lens eyeglasses having a continuous annular orbital, for example, removal of the lens such as for replacement is difficult and often impossible for the end user. Accordingly, there remains a need for further improvement in various aspects of eyeglass lens retention mechanisms.

SUMMARY

Several advantageous features can be present in embodiments of eyewear, such as an eyeglass or goggle, that incorporates one or more of the features disclosed herein. While these features may be illustrated with regard to a dual lens eyeglass, these features can also be incorporated into unitary lens eyewear or into a goggle. Accordingly, the present discussion and embodiments are intended to illustrate features that can be applied to dual or unitary lens eyeglasses or goggles, although illustration and discussion will be shown for dual lens eyeglasses for the sake of brevity. Thus, goggle embodiments can be provided which include the advantageous features disclosed herein. As used herein, in accordance with the customary understanding in this art, the term "eyeglass" and similar terms include products with glass or non-glass lens that are corrective or non-corrective.

Some eyeglass and goggle lenses are distorted or deformed from their original as-molded or pre-mounted geometry when mounted in the eyeglass or goggle. Thus, one or more optical aberrations can be created in the lens, which degrades the optical performance of the lens. In order to address this and other problems of the prior art, some embodiments disclosed herein provide for unique solutions that allow a lens to be removably or permanently mounted in eyewear such that the lens is not excessively deformed and therefore maintains superior optical qualities.

Further, a continuing objective in the field of high performance eyewear, particularly for eyewear which is intended for use in high-speed action sports or military applications, is ballistic resistance and lens stability. Various improvements have been made that enable a wearer to quickly modify eyewear using replaceable components and/or lenses, such by using the systems disclosed in U.S. Pat. Nos. 4,730,915, 5,387,949, and 7,347,545, the entirety of the disclosure of each of which is incorporated herein by reference. In some embodiments disclosed herein, additional support can be provided to a replaceable or removable lens in order to enhance the ballistic resistance and lens stability of an eyeglass or goggle. Some examples of support features are shown in Applicants' U.S. Patent Application Publication No. 2010/0085533, published on Apr. 8, 2010, now U.S. Pat. No. 7,954,942, issued on Jun. 7, 2011, the entirety of which is incorporated herein by reference. Further examples of support features are shown in Applicants' copending U.S. Patent Application Publication No. 2011/0007262, published on Jan. 13, 2011, U.S. application Ser. No. 13/020,747, filed on Feb. 3, 2011, and U.S. application Ser. No. 13/051,913, filed on Mar. 18, 2011, the entireties of each of which are incorporated herein by reference.

In some embodiments, at least in part, a durable eyeglass or goggle design can enable the lens to be securely retained by the frame of the eyeglass or goggle using one or more lens retention mechanisms or devices. Further, a lens of the eyeglass or goggle can comprise corresponding engagement features that enable the lens to be coupled to the frame.

In some embodiments, in response to the application of a force, such as a ballistic event (such as an impact from a projectile and/or blunt contact with an object), the retention mechanism can advantageously constrain the lens from excessive translational and/or rotational movement in one or more (or all) directions when the lens is engaged and/or supported by the retention mechanism. In some embodiments, the eyewear may permit transitory movement, but the eyewear can be configured to diminish or substantially or entirely prevent transitory movement due to ballistic forces (e.g., permit temporary, minor movement after which the lens generally returns to its original position). In some embodiments, the eyewear can be configured to diminish or substantially or entirely prevent impact failure of the lens or eyewear component(s) (e.g., prevent the lens or eyewear component(s) to from being separated from the eyeglass). In some embodiments, both transitory movement and impact failure may be generally prevented.

Some embodiments can advantageously securely retain the lens relative to the frame while generally preserving optimal optical characteristics (e.g., without undermining, diminishing, or ruining the optical characteristics of the lens). For example, the lens can be secured to and/or supported by the frame in a manner that generally preserves the as-molded geometry of the lens. Moreover, embodiments disclosed herein can advantageously provide an eyeglass or goggle in which the lens can be easily removed and replaced by the wearer while enabling the wearer to mount the lens while providing superior ballistic resistance and lens stability.

To achieve some of the above-noted benefits, some embodiments provide an eyeglass or goggle frame that can support at least one lens in a field of view of a wearer. The frame can comprise lens retention means for securing the lens relative to the frame. The lens retention means can comprise one or more retention mechanisms. The retention mechanism can comprise a stationary or passive retention mechanism and/or a movable or active retention mechanism for securing the lens relative to the frame and/or engaging the lens.

Further, some embodiments can comprise one or more lenses having at least one engagement portion. The engagement portion(s) of the lens can have a shape that is generally complimentary to a corresponding retention mechanism(s), engagement structure(s), or restraining portion(s) of the frame so that the lens and the frame can closely fit together. For example, the engagement portion(s) of the lens can comprise a recess, protrusion, aperture, detent, peripheral cutout, or other engageable structure. The retention mechanism(s), engagement structure(s), or restraining portion(s) of the frame can engage the engagement portion(s) of the lens for securing the lens relative to the frame.

For example, some embodiments can be configured to comprise one or more stationary or passive lens retention mechanisms and/or one or more moveable or active lens retention mechanisms. Some embodiments can include two moveable or active lens retention mechanisms. In embodiments having two or more lens retention mechanisms, the lens retention mechanisms can be spaced apart from each other. For example, the lens retention mechanisms can be located on generally opposite sides of lens-holding region(s) of the frame. Further, the lens retention mechanisms can interact with opposing sides or ends of the lens(es). For example, in a dual lens eyeglass, one of the retention mechanisms can be located along a nosepiece or bridge of the frame while the other retention mechanism is located adjacent to a lateral side of the frame, such as adjacent to a coupling between the frame and an earstem of the eyeglass.

In some embodiments, the eyeglass or goggle can comprise a stationary or passive lens retention mechanism. The stationary or passive lens retention mechanism can comprise an engagement portion of the lens that can be configured to engage with a lens catch of the frame. For example, the lens catch can comprise an aperture, protrusion, or recess that can engage with a complementary engagement portion of the lens when the lens is positioned in the lens slot. The complementary engagement portion of the lens can comprise a recess, protrusion, aperture, detent, peripheral cutout, or other engageable structure in a body of the lens. The lens catch can restrain one or more degrees of freedom of movement of the lens.

In some embodiments, the eyeglass or goggle can comprise a movable or active lens retention mechanism. The active lens retention mechanism can be configured as a latch device for engaging an engagement portion of the lens to secure the lens relative to the frame. The latch device can comprise an engagement structure that is movable between a disengaged position and an engaged position for restraining movement of the lens. The engagement structure of the latch device can directly or indirectly engage with an engagement portion of the lens and restraining movement of the lens.

For example, the engagement structure of the latch device can be movable relative to the lens to define a path of motion that converges toward the lens. In some embodiments, the path of motion can be generally oblique relative to a surface of the lens adjacent to the engagement portion of the lens. For example, the path of motion can be oriented relative to the surface of the lens adjacent to the engagement portion of the lens at an angle of between at least about 5° and/or less than or equal to about 60°. Further, the path of motion can be oriented relative to the surface of the lens adjacent to the engagement portion of the lens at an angle of between at least about 10° and/or less than or equal to about 45°. In some embodiments, the path of motion can be oriented at an angle between at least about 20° and/or less than or equal to about 30°. In some embodiments, the path of motion can be oriented at an angle of about 27° relative to the surface of the lens. Further, the relative angle of the path of motion can be measured against an arcuate lens based on a tangent line at or adjacent to the intersection the lens and engagement structure or a line defined by the path of the engagement structure.

The engagement structure of the latch device can be movable relative to the lens to define a path of motion that intersects with a structural feature, such as a slot, aperture, detent, protrusion, and the like of the lens to facilitate engagement of the latch device with or relative to the lens. In some embodiments, the latch device can provide direct contact with the lens to assist in retaining the lens. However, other embodiments are provided in which the latch device provides indirect contact with the lens to assist in retaining the lens, such as through intermediate components.

In some embodiments, the path of motion of the engagement structure of the latch device can be generally linear. In other embodiments, the path can be generally curvilinear. The engagement structure can also translate along the path of motion.

In some embodiments, the latch device can comprise a plurality of interconnected components. For example, some embodiments of the latch device can comprise a crank arm and a slider arm. The crank arm can be rotatably connected to the frame and to the slider arm. This rotatable connection can be a pivot or hinge-type or a ball-and-socket-type connection. In some embodiments, the crank arm can rotate about a generally horizontal axis relative to the frame. The crank arm and the slider arm can form a slider-crank assembly by which the engagement structure is both slidably and rotatably movable relative to the frame and/or the lens to engage or disengage with the lens.

In some embodiments, the frame can comprise a guide slot formed therein. The guide slot can be configured to guide or control the movement of the engagement structure of the latch device. The guide slot can be configured such that the engagement structure of the latch device can be directly or indirectly connected with the guide slot. For example, the guide slot can engage with another component that is coupled to the engagement structure. However, the guide slot can also be directly engaged with the engagement structure. Further, the guide slot can be configured as an elongate slot extending in an anterior-posterior direction along the frame.

The engagement structure of the latch device can be configured to extend through the guide slot of the frame. The engagement structure can also engage with the engagement portion of the lens while extending through the guide slot of the frame. In such embodiments, the latch device can couple the lens relative to the frame.

For example, the engagement structure of the latch device can be disposed through and movable within the guide slot for moving between the engaged and disengaged positions for securing the lens relative to the frame. Alternatively, the engagement structure can be linked to another structure of the latch device that can be received within the guide slot. The interaction of the guide slot and the latch device can facilitate alignment of the latch device relative to the frame and relative to an engagement portion of the lens. Thus, the guide slot of the frame can provide controlled movement of the engagement structure relative to the frame and the lens.

Further, in some embodiments, the frame can comprise one or more support walls. The support wall(s) can be configured to extend along at least a portion of the lens when the lens is fitted against the frame. Further, the support wall(s) can be configured such that the lens is interposed between a pair of support walls or between a support wall and another portion of the frame.

In embodiments wherein the frame comprises a guide slot, the guide slot can be disposed through the support wall(s). For example, the frame can comprise a guide slot that extends along at least a portion of a support wall which is positioned or used to support a portion of the lens.

The engagement portion of the lens can be configured to engage with the latch device for preventing the lens from separating from the frame. The engagement portion of the lens can comprise an elongate aperture extending through the lens. The aperture can extend in a generally horizontal direction when the lens is coupled to the frame. The engagement structure of the latch device can comprise a protrusion that is movable into the aperture of the lens for securing the lens relative to the frame.

In some embodiments, the eyeglass can be configured such that an aperture of the lens can be aligned with a guide slot formed in a support wall of the frame, which can be used to guide movement of the latch device. In such an embodiment, the latch device can be aligned with the aperture of the lens due to the interaction between the guide slot of the frame and the engagement structure of the latch device. Accordingly, the engagement structure of the latch device can be passable through a support wall of the frame to engage the engagement portion of the lens upon movement of the latch device from the disengaged position to the engaged position.

In dual lens embodiments, the frame can comprise first and second lens supports. Each lens support can comprise a lens retention mechanism for supporting first and second lenses in the field of view of the wearer. Various features discussed above can be incorporated into the frame and the lenses in order to ensure retention of the lenses by the frame.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

While the present description sets forth specific details of various embodiments, it will be appreciated that the description is illustrative only and should not be construed in any way as limiting. Additionally, although particular embodiments of the present inventions may be disclosed or shown in the context of unitary or dual lens eyewear systems, such embodiments can be used in both unitary and dual lens eyewear systems. Further, although embodiments disclosed herein can be used with eyeglasses, such embodiments can also be used with goggles. Embodiments are illustrated and discussed generally with respect to dual lens eyeglasses for sake of brevity, though such embodiments can be used with unitary or dual lens eyeglasses or goggles.

Further, although particular embodiments may be disclosed or shown in the context of eyeglass or goggle frames having partial orbitals, such embodiments can be used with frames having either full or partial orbitals. Retention components and structures in accordance with embodiments disclosed herein can also be utilized to retain one or more lenses (dual or unitary) of a goggle, such as a ski goggle or motocross goggle. The retention mechanisms may be utilized either as the primary connector or as a secondary connector for cooperation with another lens retention mechanism or system. Furthermore, various applications of such embodiments and modifications thereto are also encompassed by the general concepts described herein.

Figure 1:
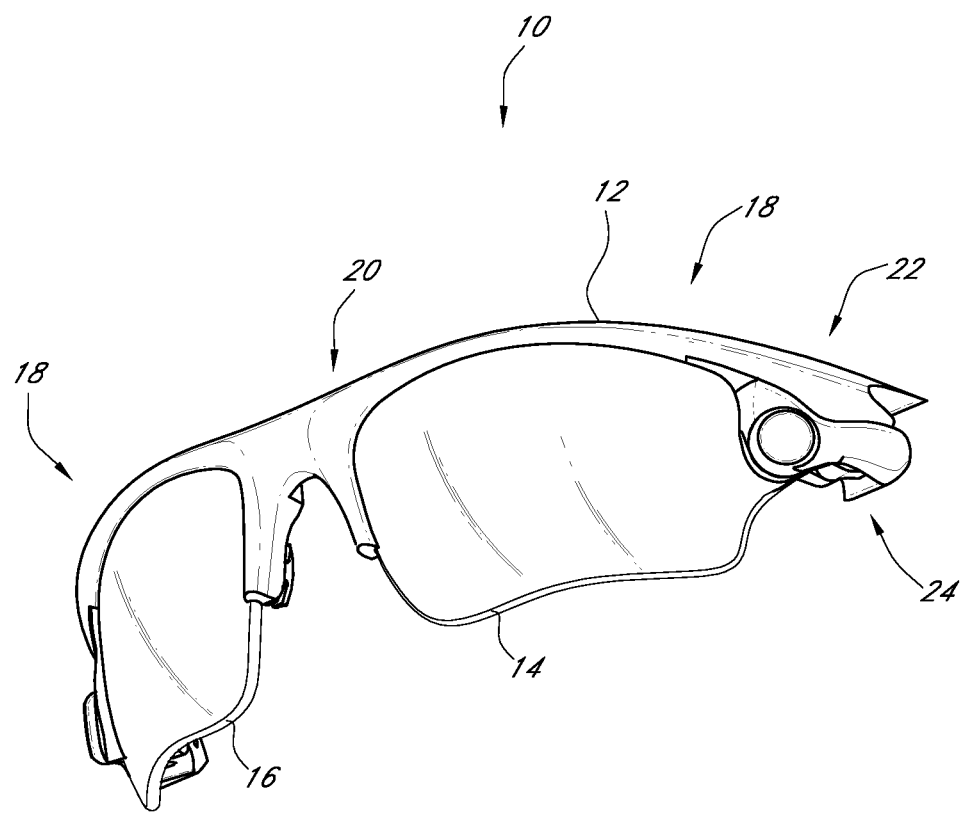
FIG. 1 is a front perspective view of an eyeglass in accordance with an embodiment of the present inventions.

FIGS. 1-18 illustrate an embodiment of the present inventions. Referring to FIG. 1, the illustrated embodiment comprises an eyeglass 10 having a frame 12 and at least one lens 14. In this embodiment, the eyeglass 10 comprises a pair of lenses 14, 16 that are supported by partial orbitals 18 of the frame 12. The frame 12 comprises a nosepiece section disposed intermediate the partial orbitals 18.

Additionally, the eyeglass 10 can comprise at least one lens retention mechanism. In some embodiments, such as that illustrated in the figures, each lens can be secured to the frame by first and second cooperating lens retention mechanisms, spaced apart from each other and disposed adjacent to the frame-lens interface. In a dual lens system such as that shown in FIG. 1, the frame 12 can comprise a first retention section 20 at a medial aspect of the lens and a second retention section 22 at a lateral aspect of the lens. The lens 14 can be supported relative to the frame 12 by cooperating lens retention mechanisms in the first retention section 20 and the second retention section 22.

The lens retention mechanisms can comprise one or more stationary or passive retention mechanisms and/or one or more movable or active retention mechanisms for engaging the lens 14. In a stationary or passive retention mechanism, engagement can occur between interlocking structures of the frame and the lens upon the lens being fitted against a portion of the frame. For example, a notch in a perimeter of the lens can fit onto a protrusion in a groove of the frame without requiring other or moveable components to limit one or more degrees of freedom of movement of the lens relative to the frame. In a movable or active retention mechanism, engagement can occur after the lens is fitted against the frame by moving a locking structure from a disengaged position to an engaged position. Thus, in a movable or active retention mechanism, a separate component can be moved relative to the lens and the frame to secure the lens relative to the frame.

The retention mechanism(s) can be used for engaging with a lens, whether in a dual lens or unitary lens system. In a dual lens system of some embodiments, the frame can comprise at least one passive retention mechanism for each lens and at least one active retention mechanism for each lens. The passive and/or active retention mechanism(s) can be disposed along any portion of the boundary between the lens and the frame. In the illustrated embodiment, each lens has a passive medial connector and an active lateral connector as detailed further below.

Figure 2:
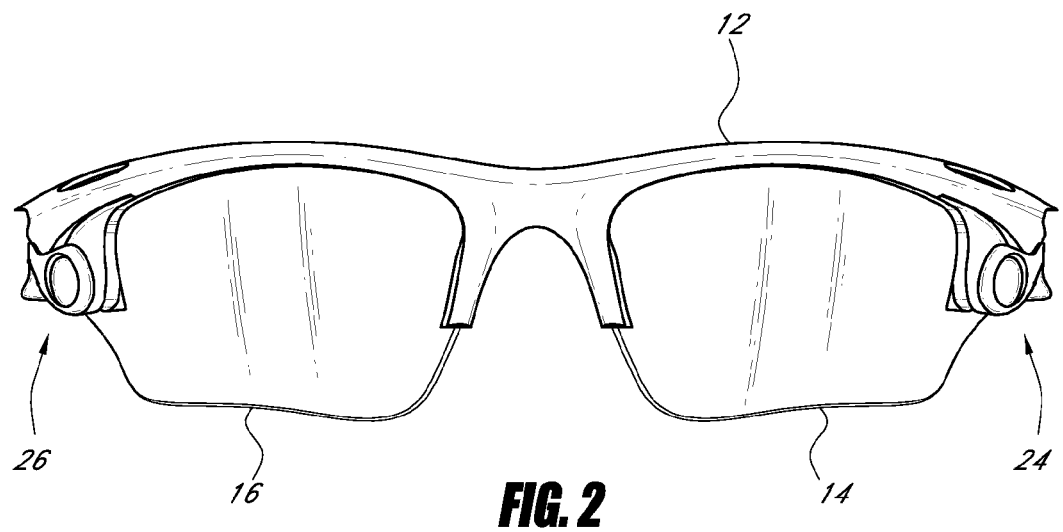
FIG. 2 is a front elevational view of the eyeglass illustrated in FIG. 1.
Figure 3:
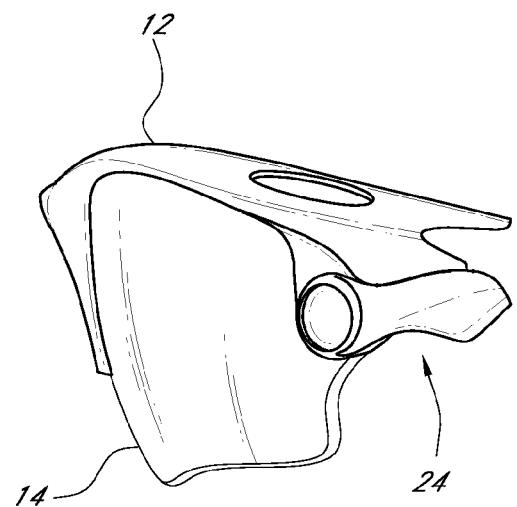
FIG. 3 is a side elevational view of the eyeglass illustrated in FIG. 1.

FIG. 2 illustrates a front elevational view of the eyeglass 10 shown in FIG. 1. As shown, the eyeglass 10 can comprise a pair of lateral connectors or active lens retention mechanisms in the form of latches 24, 26 that can be used to secure the lenses 14, 16 relative to the frame 12. The latches 24, 26 can be configured to engage and release the lenses 14, 16 in a manner that minimizes compression, deflection, or torsion of the lenses to substantially preserve optical quality in the lenses. As noted above, the latches 24, 26 are shown in a dual lens eyeglass embodiment. However, embodiments can be provided which use a unitary lens that is secured to an eyeglass frame using one or two latches, such as those shown in FIG. 2.

Figure 4:
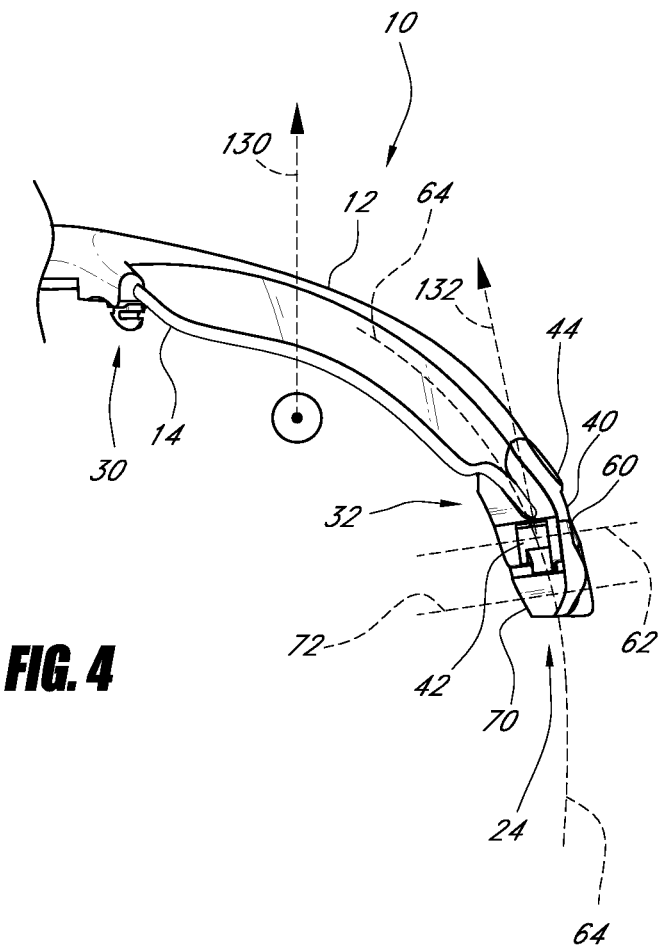
FIG. 4 is a bottom view of a portion of the eyeglass illustrated in FIG. 1.

FIG. 4 is a bottom view of the eyeglass 10 illustrating an embodiment of the latch 24. The lens 14 comprises first and second engagement sections, such as medial and lateral sections 30, 32. The latch 24 can engage with the lateral section 32 of the lens 14. The latch 24 can comprise a lever arm or slider arm 40 which is movable between a first position in which the lens 14 may be freely positioned within or removed from the lens slot, and a second position in which the lens 14 is locked within the lens slot.

In the illustrated embodiments, the latch 24 additionally comprises a crank arm 42. The crank arm 42 can be pivotally attached to the frame 12 and to the slider arm 40. Together, the slider arm 40 and the crank arm 42 can form a slider-crank assembly that permits an engagement structure 44 of the slider arm 40 to move between an engaged position 50 and a disengaged position 52. Movement of the engagement structure 44 allows the latch 24 to secure the lens 14 relative to the frame 12 or allows disengagement of the lens 14 from the frame 12.

Figure 5:
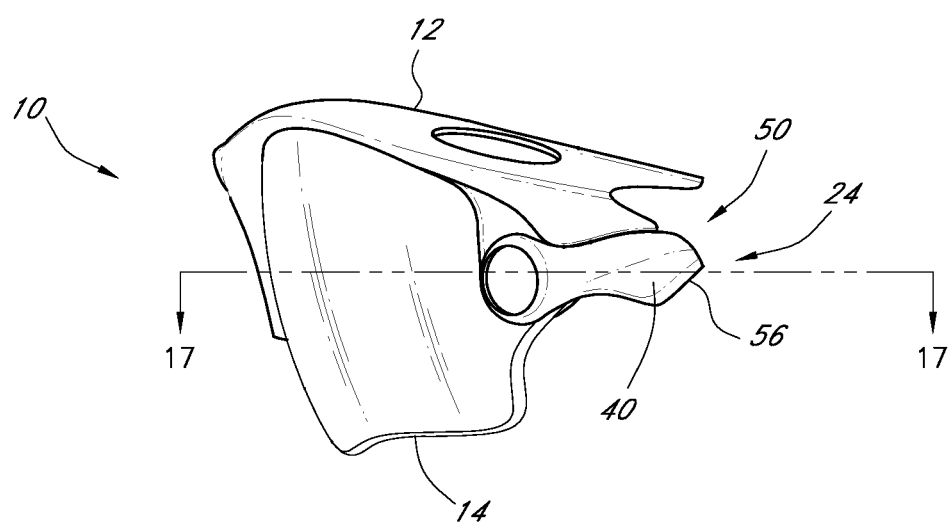
FIG. 5 is a side view of the eyeglass illustrated in FIG. 1, wherein a latch device thereof is shown in an engaged position, according to an embodiment.
Figure 6:
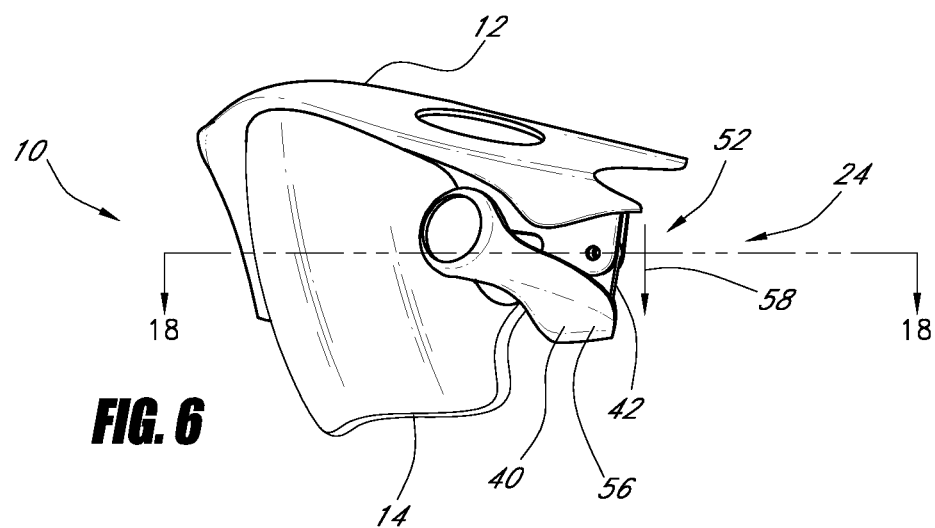
FIG. 6 is a side view of the eyeglass illustrated in FIG. 1, wherein a latch device thereof is shown in a disengaged position, according to an embodiment.
Figure 7:
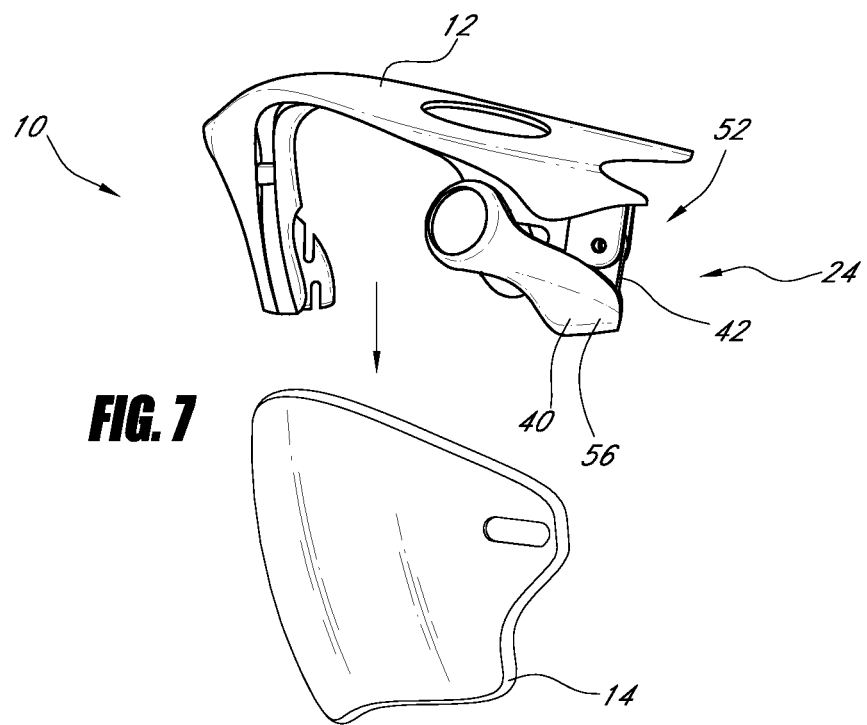
FIG. 7 is a side view of the eyeglass illustrated in FIG. 1, wherein a latch device thereof is shown in a disengaged position and a lens thereof is separated from the eyeglass, according to an embodiment.

Referring now to FIGS. 5-7, the latch device 24 is shown in the engaged position 50 (FIG. 5) and the disengaged position 52 (FIGS. 6-7). In this embodiment, a posterior end 56 of the slider arm 40 is urged downwardly in the direction shown by the arrow 58 of FIG. 6. Due to the rotational coupling of the posterior end 56 of the slider arm 40 with the crank arm 42, the posterior end 56 of the slider arm 40 moves through an arcuate path and causes the engagement structure 44 to advance forward from a first or posterior position to a second or anterior position.

In the illustrated embodiment, the engagement structure 44 follows a substantially linear path 132 which is oriented at least about parallel and/or at an angle of less than or equal to about 45° relative to the anterior-posterior axis or straight-ahead line of sight. As used herein, the wearer's normal or straight ahead line of sight shall refer to a line projecting straight ahead of the wearer's eye, with substantially no angular deviation in either the vertical or horizontal planes as illustrated for example by line 130 in FIG. 4; the straight ahead line of sight can also be oriented generally parallel relative to an optical center line of the lens 14. In some embodiments, the path 132 can be oriented at an angle of at least about 5° and/or less than or equal to about 30° relative to the straight ahead line of sight. Further, the path 132 can be oriented at an angle of at least about 10° and/or less than or equal to about 15° relative to the straight ahead line of sight. In some embodiments, the path 132 can be oriented at an angle of about 12° relative to a straight ahead line of sight.

Further, the engagement structure can comprise or support a projection 78 (see FIG. 11) for engagement within a corresponding aperture 124 in the lens when the slider arm 40 is in the engaged position 50. The projection 78 can follow or define the same path as the path 132 of the engagement structure 44 (and for simplicity is also shown as line 132 and FIG. 4). Thus, as the slider arm 40 is pivoted into the disengaged position 52, the projection 78 can move anteriorly and out of engagement with the lens aperture 124. As shown in FIG. 7, the lens 14 can be removed from engagement with the frame 12 when the latch is in the disengaged position 52.

Figure 17:
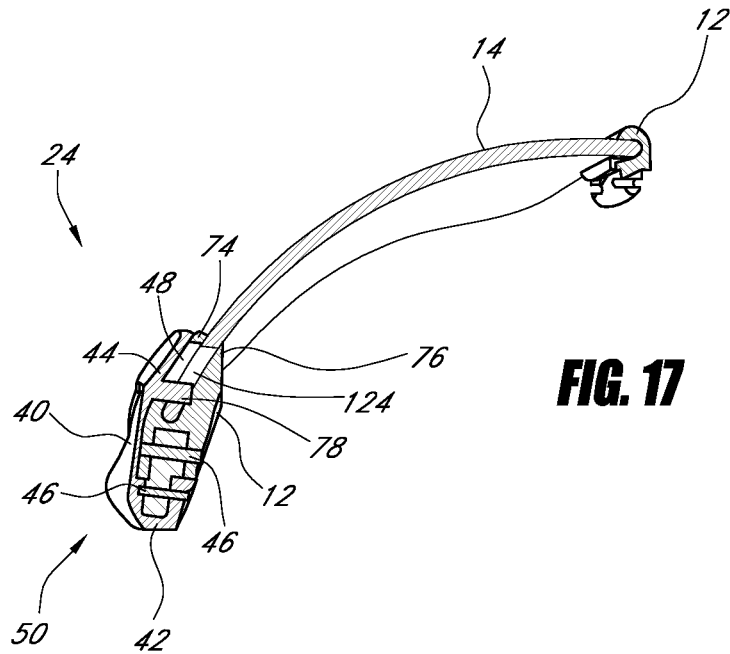
FIG. 17 is a cross-sectional top view of the eyeglass of FIG. 1 taken along lines 17-17 of FIG. 5, wherein the latch device is in the engaged position, according to an embodiment.
Figure 18:
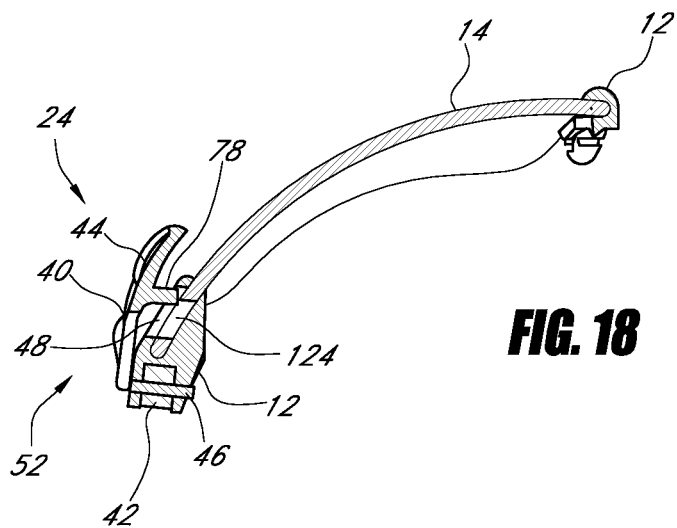
FIG. 18 is a cross-sectional top view of the eyeglass of FIG. 1 taken along lines 18-18 of FIG. 6, wherein the latch device is in the disengaged position, according to an embodiment.

The axis of motion or path 132 of the projection 78 on engagement structure 44 can be oriented to intersect with the aperture 124 along a top, bottom, or side edge of the lens 14. The path 132 can be oriented in the horizontal plane generally tangential (or generally parallel to a tangent) to the horizontal arc which intersects the front lateral surface or engagement portion (aperture or projection) of the lens 14 as shown in FIGS. 4 and 17-18. As noted above, the path 132 of the projection 78 can also be oriented generally parallel or at an angle relative to the straight ahead line of sight. For example, as discussed further below, in some embodiments, the projection 78 can move in a path that is oriented at an acute angle with respect to an aperture of the lens such that the projection 78 engages with the aperture. In such an embodiment, movement of the projection 78 in a path that diverges only minimally from the surface of the lens can permit engagement or disengagement of the lens. The designs discussed herein can thereby advantageously provide a more compact design while providing a robust structure that reduces the obtrusion of components.

For example, with reference to FIG. 4, the crank arm 42 can optionally be coupled to the frame 12 at a first joint 60 that defines a rotational axis 62 extending generally horizontally relative to the frame 12. The rotational axis 62 can extend generally normal to an arc 64 that follows the curvature of the lens 14. Accordingly, upon rotation of the crank arm 42, the projection 78 can move along a path that intersects with the arc 64 of the lens 14, as shown in FIG. 4. In this manner, the engagement structure 44 can be displaced toward or away from the arc 64, thus enabling the engagement structure 44 to engage with the lens 14.

The crank arm 42 can be coupled to the slider arm 40 such that the crank arm 42 and the slider arm 40 form a second joint 70 that defines a rotational axis 72. The rotational axis 72 can be oriented generally parallel relative to the rotational axis 62, as shown in FIG. 4. Alternatively, the rotational axis 72 can be oriented in a non-parallel or angled configuration relative to the rotational axis 62.

Further, some embodiments can be configured to comprise a rotating engagement structure or latch device that rotates about an axis such as the axis 72 shown in FIG. 4. In such embodiments, the latch can comprise a single body or component that is pivotally mounted to the frame 12 at a first end and that comprises a second end that rotates about the axis (such as axis 72), wherein the second end has an engagement portion or connector (such recess, protrusion, aperture, detent, peripheral cutout, or other engageable structure, including projection 78) to engage the lens. In use, the latch can rotate from a disengaged position to an engaged position in which the connector is engaged with a corresponding recess or projection disposed on a lateral side of the lens. Further, in such embodiments, and engagement portion of the lens may extend in a generally vertical or sloping direction (instead of the generally horizontal shape or orientation of the aperture 124 shown in FIGS. 7-8). Further, the engagement portion, such as a recess, protrusion, aperture, detent, peripheral cutout, or other engageable structure, can be formed to extend from a periphery of the lens inwardly. For example, the engagement portion can extend from a top edge of the lens downwardly towards a lower edge of the lens, having an endpoint that is located closely to a midpoint between the top edge and the lower edge of the lens. Further, in some embodiments, the engagement structure of the lens can extend downwardly from a top edge of the lens, having an endpoint that is positioned vertically lower relative to the rotational axis of the latch device such that the latch device must be rotated from a generally vertical orientation (disengaged position) downwardly until the longitudinal axis of the latch device passes through a horizontal plane (passing through the rotational axis of the latch device) to the engaged position. Finally, the latch device can be biased toward the engaged position by means of, for example, a protrusion/recess engagement between the latch device and the frame or lens that creates a snap fit with or generally impedes rotation of the latch device, a spring, or biasing other structures such as those disclosed herein and/or known in the art.

In accordance with these and other embodiments disclosed herein, the lens(es) of the eyewear can comprise lateral portions that extend at an acute angle relative to the straight ahead line of sight. The lateral portions can provide an engagement area for engaging with the lens retention mechanism of the eyewear. In some embodiments, the lateral portions of the lens can comprise lateral portions of an arcuate lens, in which the lateral portions define a surface or a surface having a tangent that extends and an acute angle relative to the straight ahead line of sight. Embodiments of such a lens are illustrated, for example, in FIG. 4.

Referring again to FIG. 4, in some embodiments, the first and/or second joints 60, 70 can be configured to provide multi-planar movement. For example, the first and/or second joints 60, 70 can comprise a ball-and-socket joint that allows the slider arm 40 and the crank arm 42 additional degrees of freedom of movement relative to the frame 12.

In some embodiments, the crank arm 42 can be coupled to the frame 12 and pivot about a rotational axis that extends generally vertically relative to the frame 12. The crank arm 42 can enable the slider arm 40 to move between an engaged position and a disengaged position relative to the lens 14. The generally vertical rotational axis can extend upwardly through the frame 12 or be spaced at a distance anterior or posterior relative to the frame 12.

Optionally, the latch device can exhibit preferential motion towards the engaged or disengaged position. Any of a variety of biasing structures can be used with such embodiments. For example, the latch can comprise a linear compression spring that urges the latch device toward the engaged or disengaged position. The latch can also comprise a rotational biasing mechanism, such as a coil spring urging rotational movement of a component of the latch about a pivot axis thereof. The latch can also comprise a tab or gripping portion that can be actuated by the wearer in order to move the latch device toward the disengaged position, thereby enabling removal of the lens from the eyeglass. Once the latch is advanced a small distance in the direction of the other position, it is based to 'snap' the rest of the distance to the other position.

Figure 9:
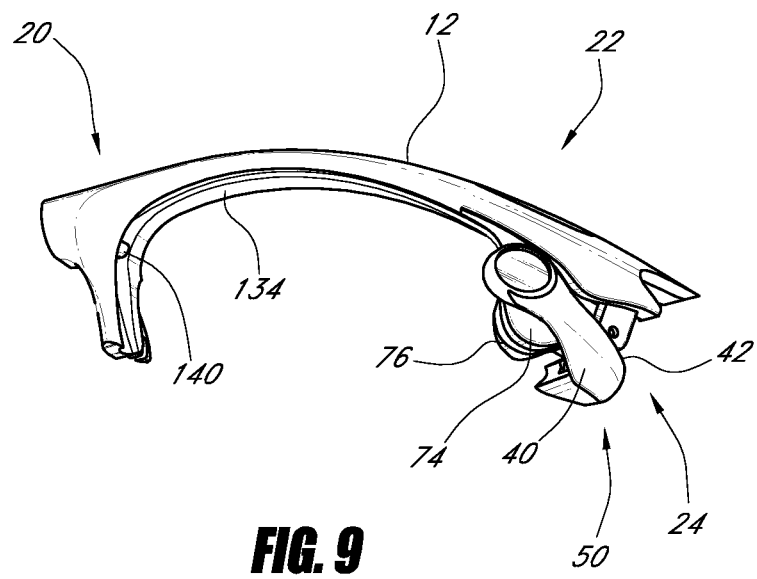
FIG. 9 is a front perspective view of a portion of a frame of the eyeglass of FIG. 1, illustrating the latch device in the disengaged position.
Figure 10:
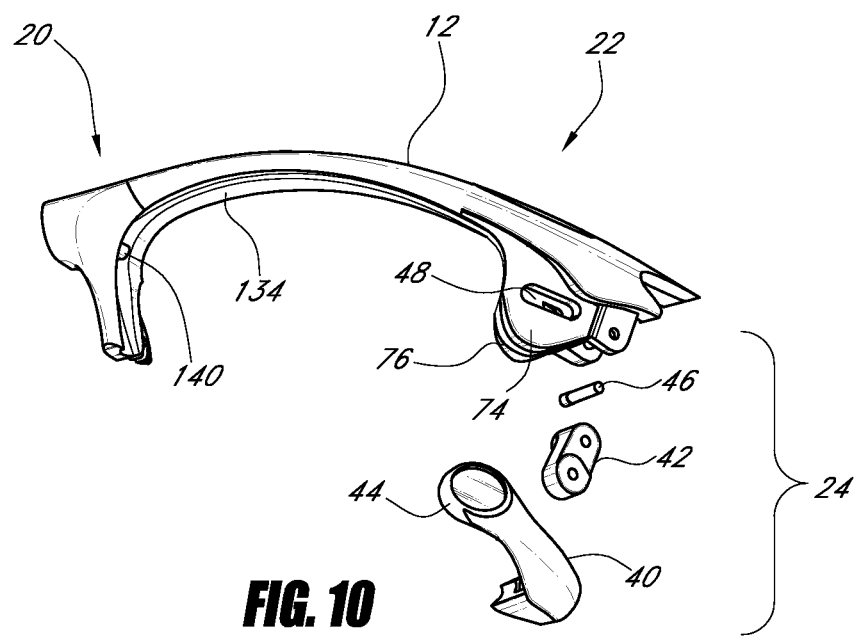
FIG. 10 is a front perspective view of a portion of a frame of the eyeglass of FIG. 1, illustrating an exploded view of the latch device in the disengaged position.

FIG. 10 illustrates the latch 24 in an exploded view in which the latch 24 is shown in the disengaged position 52. The latch 24 can comprise a plurality of interconnected articulating components that facilitate movement of the engagement structure 44 relative to the frame 12 and the lens 14. For example, as shown in FIGS. 9-10, the device 24 comprises the slider arm 40 and the crank arm 42. The slider arm 40 and the crank arm 42 can be pivotally interconnected using one or more screws or pins 46. The crank arm 42 can also be pivotally connected to the frame by a screw or pin 46. In some embodiments, as illustrated in FIGS. 9 and 10, one or more portions of the slider arm 40 that are configured to be a pushing surface or otherwise moved by the fingers or thumb can be angled and can be substantially wider than an intermediate portion of the slider arm 40. For example, as illustrated, the top and bottom surfaces of the lateral end of the slider arm are angled and substantially wider than the rest of the slider arm 40, and may be provided with a surface texture, ridges or other friction enhancing surface structures.

The lens retention system can additionally comprise a tracking mechanism to assist in aligning movable portions throughout the range of motion. The tracking mechanism can cause the engagement structure 44 to move along a path having a desired path of motion into or out of engagement with the lens 14. For example, the tracking mechanism can cause the engagement structure 44 to move along a generally linear path. The tracking mechanism can alternatively cause the engagement structure 44 to move along an arcuate planar or three-dimensional path into or out of engagement with the lens 14.

In some embodiments, the tracking mechanism can be configured such that the slider arm 40 interacts with or engages with a portion of the frame 12 to cause the engagement structure 44 to move in a desired path. For example, the tracking mechanism can comprise a guide slot 48 formed in the frame 12. The guide slot 48 can be formed in the frame 12 at the second retention section 22. In the embodiment of FIG. 10, the second retention section 22 can comprise anterior and posterior sidewalls or flanges 74, 76, spaced apart to receive the lens in between. The guide slot 48 can be formed in the anterior flange 74. However, some embodiments can be configured without anterior and posterior flanges 74, 76 between which the lens is fitted. For instance, the lens retention means can be configured to provide an interference fit with a portion of the lens between the frame and a peripheral edge of the lens.

Figure 11:
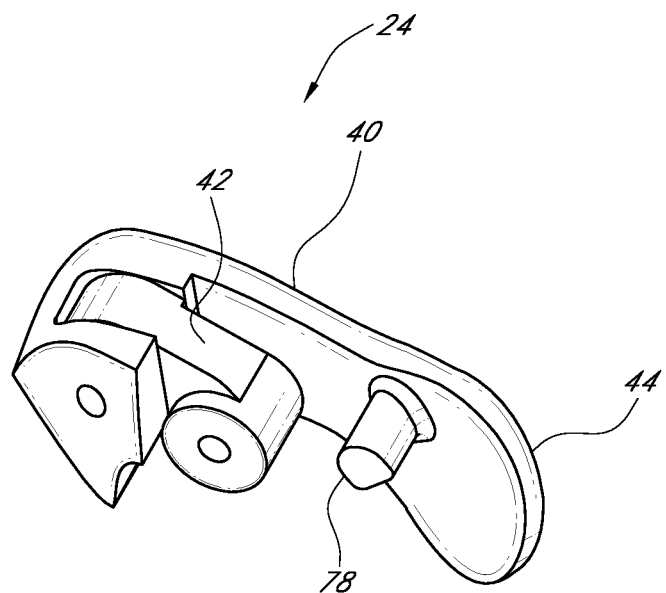
FIG. 11 is a top perspective view of components of the latch device of the eyeglass illustrated in FIG. 1.
Figure 12:
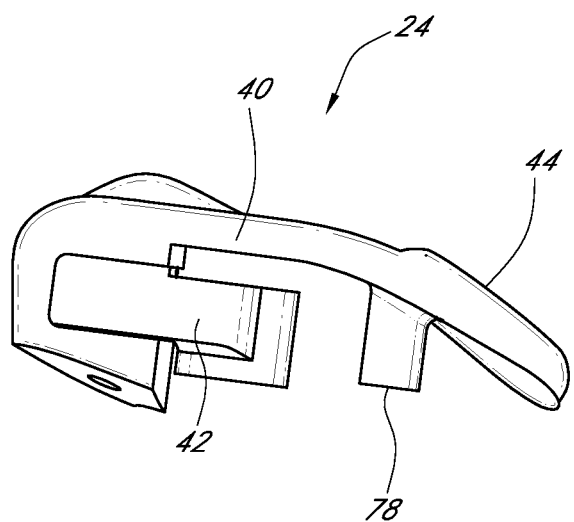
FIG. 12 is a top plan view of components of the latch device of the embodiment of the eyeglass illustrated in FIG. 1.

As illustrated in FIGS. 11-12, the engagement structure 44 of the slider arm 40 can comprise a projection 78. The projection 78 can be positioned within the guide slot 48 when the latch device 24 is assembled with the frame 12. Accordingly, as the latch device 24 moves between the engaged position 50 and the disengaged position 52, the projection 78 can advance back and forth within the slot 48. The tracking of the projection 78 is also shown in FIGS. 13-18. Thus, the rotation of the slider arm 40 and the crank arm 42 can be converted to linear movement of the projection 78 within the slot 48.

The tracking of the projection 78 within the guide slot 48 thus not only facilitates alignment of the engagement structure 44 relative to the frame 12 throughout its range of motion, but as discussed further herein, enables the lens to be repeatably engaged and disengaged relative to the frame 12. At one end of the slot, the projection 78 extends completely through the slot and into engagement with the lens 14. At the other end of the slot, the projection has retracted out of engagement with the lens.

However, in some embodiments, the tracking mechanism can be formed by engagement between the guide slot 48 and another portion of the latch 24, with the projection 78 being indirectly contacted or controlled through engagement with the guide slot 48.

Figure 13:
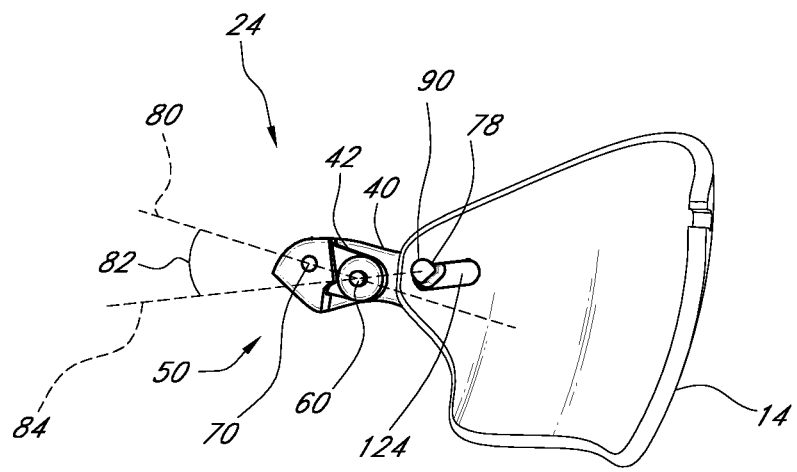
FIG. 13 is a side view of the latch device and lens of the eyeglass of FIG. 1, wherein the latch device is in the engaged position, according to an embodiment.
Figure 14:
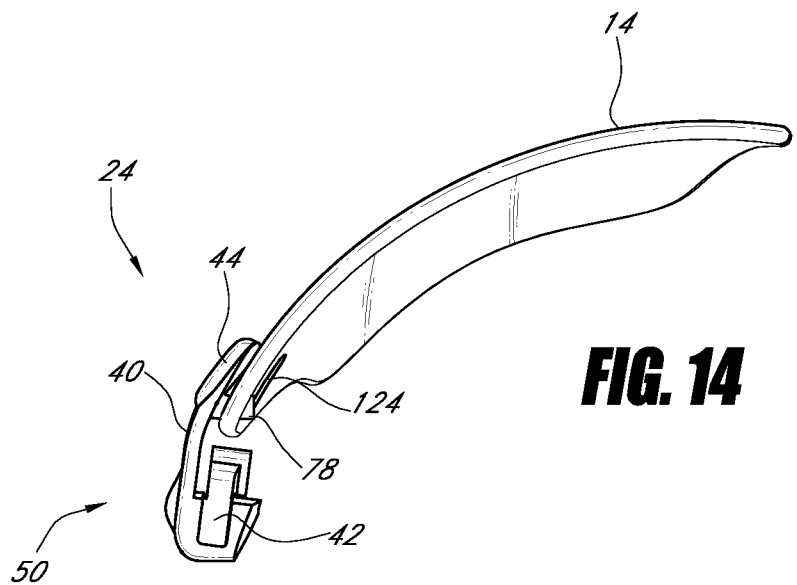
FIG. 14 is a top view of the latch device and lens of the eyeglass of FIG. 1, wherein the latch device is in the engaged position, according to an embodiment.
Figure 15:
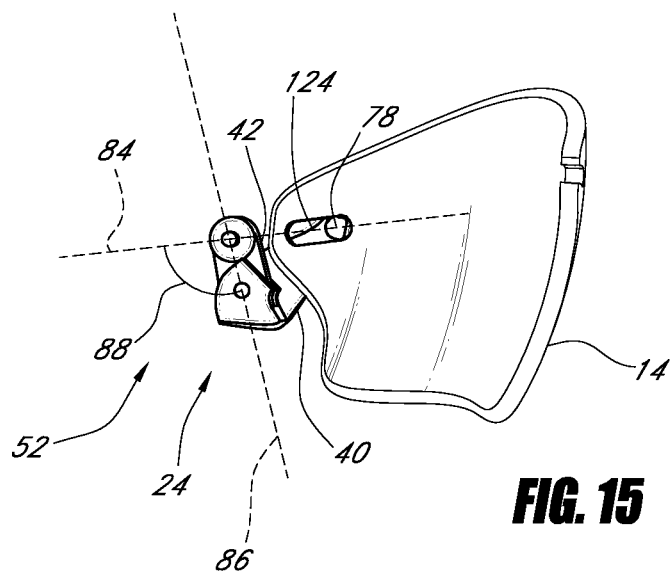
FIG. 15 is a side view of the latch device and lens of the eyeglass of FIG. 1, wherein the latch device is in the disengaged position, according to an embodiment.

FIG. 13 illustrates the crank arm 42 of a latch 24 in the engaged position 50, and FIG. 15 illustrates the crank arm 42 in the disengaged position 52. In the engaged position 50, the crank arm 42 can be disposed along a first longitudinal axis 80. As shown in the side view of FIG. 13, the first longitudinal axis 80 can be oriented at a first angle 82 relative to an anterior-posterior (A-P) axis 84. In the disengaged position 52, the crank arm 42 can be disposed along a second longitudinal axis 86. The second longitudinal axis 86 can be oriented at a second angle 88 relative to the A-P axis 84.

In some embodiments, the crank arm 42 is provided with structure or material that provides resistance to rotation such as while traversing the A-P axis 84. For example, during rotation from the engaged position 50 to the disengaged position 52, or from the disengaged position 52 to the engaged position 50, the crank arm 42 may tend to resist additional rotation as the crank arm 42 passes through the middle portion of its range of motion. The crank arm 42 can therefore tend to stay oriented or biased at either the engaged position 50 or the disengaged position 52 once the crank arm 42 achieves the respective position. Therefore, the latch 24 can be configured to avoid unintentional disengagement from the lens 14.

The mechanism for causing preferential motion or biasing of the latch 24 toward the engaged position 50 or the disengaged position 52 can comprise a variety of structures. These structures can create a preferential toggle point and may incorporate resilient, deflectable components, and/or may provide a bias in the direction of either or both of the engaged and disengaged positions.

For example, the latch 24 can be biased using a biasing component, such as a spring. The spring can be a torsional spring that is positioned along one of the axes of rotation of the components of the latch 24. The spring can also be a linear compression spring that urges the latch 24 toward the engaged position 50.

The means for causing preferential motion of the latch 24 can also comprise resilient, deflectable components of the latch 24 that interact with each other, the frame 12, and/or the lens 14 in order to create a toggle point.

For example, of the distances between the first joint 60, the second joint 70, and a bottom position 90 of the engagement structure 44 can be adjusted to cause deflection of one or more components of the latch 24 when the crank arm 42 of the latch 24 is being rotated past the A-P axis 84. In some embodiments, the location of the first joint 60 can be fixed at a distance from the bottom position 90 such that the distance between the second joint 70 and the bottom position 90 is less than the sum of the distances between the first joint 60 and the second joint 70 and between the first joint 60 and the bottom position 90. Thus, in some embodiments, the only manner of passing through the axis 84 is to cause slight resilient deflection in one or more components of the latch 24 such that the distance between the second joint 70 and the bottom position 90 is made equal to the sum of the distance between the first joint 60 and the second joint 70 and the distance between the first joint 60 and the bottom position 90. After crossing the axis 84, the one or more resilient, deflectable components of the latch 24 can return to the undeflected configuration. The latch can be configured such that bending or deflection of a component of the latch can be performed cyclically, without failure.

Preferential motion of the latch 24 can alternatively be provided by one or more protrusions and/or recesses formed in one or more components of the latch 24. The protrusions and/or recesses can pass over each other during rotation of the crank arm 42 and the slider arm 40 and create resistance such that the latch 24 resists movement from the engaged position 50 and/or the disengaged position 52. The protrusions and/or recesses can be formed on opposing surfaces of the crank arm 42 and the slider arm 40. Further, the protrusion/or recesses can also be formed on opposing surfaces of the crank arm 42 and the frame 12. Furthermore, the protrusions and/or recesses can also be formed on opposing surfaces of the slider arm 40 and the frame 12.

In either dual or unitary lens embodiments of the eyeglass or goggle, the lens can comprise one or more surfaces, edges, or structures that can be engaged by the lens retention mechanism of the frame. In the dual lens embodiment shown in FIGS. 1-18, each lens can comprise at least one surface, edge, or structure that can be engaged by the lens retention mechanism of the frame. The lens retention mechanism(s) can comprise one or more active and/or passive engagement mechanisms such as those described herein. A stationary or passive lens retention mechanism can be formed between a complementary retention surface carried by the frame and a retention surface of the lens, such as the edge of a slot, notch, projection or aperture facing generally away from the frame to provide an interference fit.

For example, the lens retention means can engage a downwardly facing surface, edge, or structure on the lens to prevent the lens from disengaging with the frame. The engagement surface, edge, or structure of the lens can form the edge of an engageable aperture, slot, protrusion, recess or detent formed in the lens. The lens engagement surface can engage a complementary engagement surface carried by an aperture, recess, or projection carried by the frame.

Figure 8:
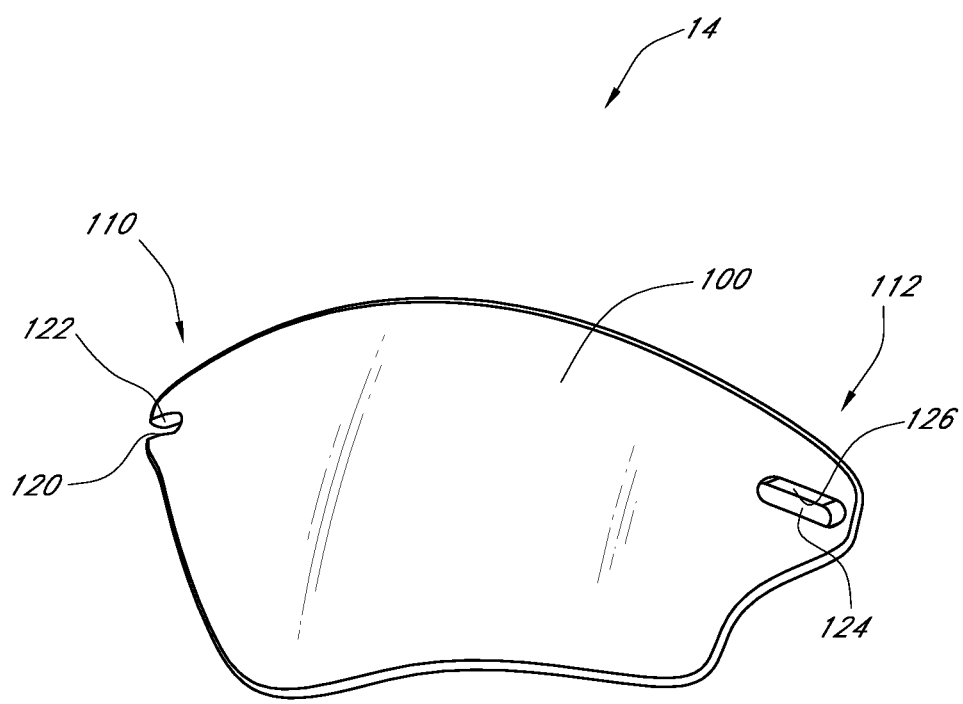
FIG. 8 is a perspective front view of a lens of the eyeglass of FIG. 1, according to an embodiment.

FIG. 8 illustrates an embodiment of a lens in a dual lens system that can be used with embodiments of the frame. The lens 14 can comprise a lens body 100, a first engagement portion 110, and a second engagement portion 112. The first engagement portion 110 can comprise a medially opening cutout or recess 120 formed along a perimeter of the lens 14. The recess 120 can comprise a generally downwardly facing retention surface 122. The second engagement portion 112 can comprise an elongated aperture 124. The elongated aperture can comprise a generally downwardly facing retention surface 126. As shown in FIGS. 7-8, a longitudinal axis of the aperture 124 can be generally horizontal or within a few degrees of horizontal. However, as noted above, some embodiments can be provided in which the aperture 124 can extend in a direction that is generally vertical or sloping relative to a horizontal plane. Further, the shape of the aperture 124 can be generally straight (as shown in FIG. 8) or arcuate in order to engage with a rotating engagement structure.

When fitted onto the frame 12, the first engagement portion 110 or recess 120 of the lens 14 can be engaged by a laterally extending projection 140 within the groove or lens slot on the frame to form a stationary or passive retention mechanism. The second engagement portion 112 or aperture 124 of the lens 14 can be engaged by the latch to form a moveable or active retention mechanism. Referring to FIGS. 9-10, the first retention section 20 of the frame 12 can be configured to engage with the first engagement portion 110 of the lens 14. The second retention section 22 can be configured to engage with the second engagement portion 112 of the lens 14.

The frame 12 typically comprises a lens slot or groove 134 extending at least partially (or substantially entirely) along the portion of the orbital of the frame 12 which contacts the lens. However, the upstanding structure or wall need not extend continuously about the orbital or frame. The groove 134 can define a cross-sectional profile configured to receive the lens 14 therein. The groove 134 can be defined by at least one sidewall disposed along the frame 12. The groove 134 can be defined by a pair of spaced apart upstanding structures or walls, such as that shown in FIGS. 9-10. The walls that define the groove 134 can provide anterior and posterior support to the lens 14. The depth of the groove can be greater, or substantially greater, than its width.

The second retention section 22 of the frame 12 can be configured such that the groove 134 is at least partially defined by a pair of wall flanges 74, 76 of the frame 12. The second engagement portion 112 of the lens 14 can be fitted into the groove 134 between the pair of flanges 74, 76. In some embodiments, the guide slot 48 of the frame 12 can be aligned with the aperture 124 of the lens 14 when the lens 14 is inserted into the groove 134 between the flanges 74, 76. Further, as discussed herein, the projection 78 of the latch 24 can extend through the slot 48 to engage with the aperture 124 of the lens 14 to secure the lens 14 relative to the frame 12.

Referring to FIGS. 13-18, articulation of the latch 24 is shown between the engaged position 50 and the disengaged position 52. As shown in the top views of FIGS. 14 and 17, when the latch 24 is moved to the engaged position 50, the projection 78 is disposed within the slot 124 of the lens 14. In this engaged position 50, the latch 24, the walls 74, 76 of the frame 12, and the projection 78 can generally restrain vertical and horizontal movement of the lens 14 relative to the frame 12. Accordingly, the lens 14 can be securely retained relative to the frame 12.

Figure 16:
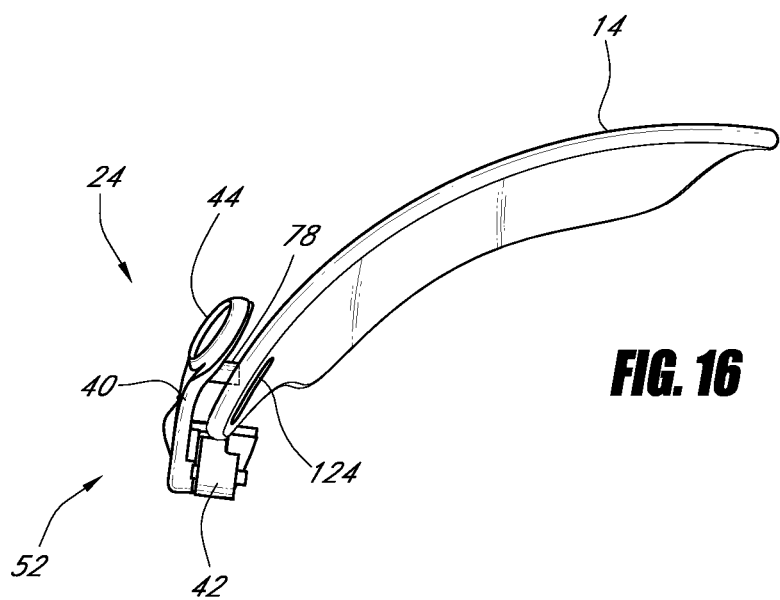
FIG. 16 is a top view of the latch device and lens of the eyeglass of FIG. 1, wherein the latch device is in the disengaged position, according to an embodiment.

The top views of FIGS. 16 and 18 illustrate that when the latch 24 is moved to the disengaged position 52, the projection 78 can be removed from the slot 124 of the lens 14. In some embodiments, the projection 78 can be entirely removed or free of the slot 124. Accordingly, the projection 78 will permit, and not generally constrain the horizontal or vertical movement of the lens 14, and the lens 14 can be removed from the frame 12. As noted above, the movement of the projection 78 out of the slot 124 can be a generally linear movement. The distance of movement or displacement of the projection 78 can be dependent on the curvature of the lens in the given cross-section of intersection between the projection 78 and the slot 124, as well as the orientation of the travel path of the projection 78 relative to the arc of the lens 14. The movement of the projection 78 can be determined by the shape and articulation of components of the latch 24. In some embodiments, the area of intersection between the engagement structure 44 (e.g., the projection 78) and the lens 14 can occur in an area of curvature of the lens 14. Such a configuration can provide a compact design in which the actuation of the latch occurs adjacent to the surface or plane of the lens or tangential to the surface of the lens. This can be provided by a pivoting or sliding latch. However, the lens can also be generally flat in that cross-section of intersection and the region of intersection between the engagement structure 44 (e.g., the projection 78) and the lens 14 can occur in a side section or lateral area of the lens 14.

For example, in some embodiments, the path of motion of the projection 78 can be generally oblique relative to a surface of the lens 14 adjacent to the slot 124 of the lens 14. For example, as illustrated in the embodiment of FIGS. 16 and 18, the path of motion can be oriented at an angle of about 27° relative to the surface of the lens 14. Nevertheless, the path of motion can be oriented relative to the surface of the lens 14 adjacent to the engagement portion of the lens 14 at an angle of between at least about 5° and/or less than or equal to about 60°. Further, the path of motion can be oriented relative to the surface of the lens 14 adjacent to the slot 124 at an angle of between at least about 10° and/or less than or equal to about 45°. In some embodiments, the path of motion can be oriented at an angle between at least about 20° and/or less than or equal to about 30°. The relative angle of the path of motion can be measured against an arcuate lens based on a tangent line at or adjacent to the intersection the lens and engagement structure or a line defined by the path of the engagement structure.

Furthermore, FIG. 17 illustrates that in the engaged position 50, the projection 78 can secure a portion of the lens 14 relative to the frame 12. As discussed above with respect to FIG. 13, some embodiments can be provided in which the latch 24 is biased toward the engaged position 50. Although not specifically shown, in some embodiments, the projection 78 can be compressed against the portion of the lens 14, exerting a force upon the lens 14, when the latch 24 is moving past a toggle point. Thereafter, once the projection 78 achieves the engaged position 50, for example, the projection 78 can be separated slightly from the portion of the lens 14 such that the projection 78 no longer exerts a force upon the lens 14. Thus, the lens 14 can be retained in a non-stressed orientation during use although a biasing mechanism of the latch may temporarily exert a force upon the lens 14 during positioning and engagement of the lens 14.

In some embodiments, the lens retention means can provide excellent ballistic resistance for the lens and the frame of the eyeglass. The lens retention means can be integrated into, carried, or supported by the frame of the eyeglass. The lens retention means can also be integrated into, carried, or supported by the lens or lenses supported by the frame. The lens retention means can also be formed as a separate part that can be retrofitted onto existing eyewear. In some embodiments, the lens retention means can restrict rotational and/or linear movement of the lens relative to the frame at one or more points of the engagement between the lens and the frame. Further, the lens retention means can comprise a portion of the frame and/or a portion formed separately from the frame that engages with a portion of the lens.

Embodiments of the eyeglass disclosed herein can tend to ensure that the lens does not become transitorily and/or permanently substantially separated from the frame in response to a ballistic event. Further, embodiments of the eyeglass can be configured such that a force transmitted to the lens is also generally transmitted to the frame of the eyeglass while substantially maintaining engagement between the lens and the frame. For example, although the lens of such an eyeglass may be damaged (cracked or chipped), the lens avoids shattering or displacing relative to the frame. This ballistic resistance can provide excellent protection to the wearer.

Additionally, the lens retention means can comprise a resilient material, such as a compressible or flexible material disposed at least along a portion of the lens retention means. For example, a protrusion, connector, body, or other structure or component of the lens retention means can be formed from or otherwise include one or more resilient materials. As a result, a ballistic event will not tend to result in damage at the interconnection between the lens retention means and the lens and/or frame. In some embodiments, a protrusion of the lens retention means can be formed from a resilient or flexible material or comprise a coating, layer, or one or more surface features formed from the resilient or flexible material. The lens retention means, such as the projection and/or the resilient or flexible material, can have a modulus of elasticity that is less than that of the lens. Further, lens retention means, such as the projection and/or the resilient or flexible material, can have a modulus of elasticity that is less than that of the frame. Accordingly, at least a portion of the lens retention means can dampen or absorb force or vibration from a ballistic event.

In some embodiments that comprise a unitary lens, the lens can be engaged and/or supported at least at both lateral sides and a central portion thereof. For example, a unitary lens may be secured to and/or supported by a frame using a first retention mechanism on the left side of midline and a second retention mechanism on the right side of midline. The retention mechanisms can include any of the passive or active retention mechanisms disclosed herein. The first retention mechanism may be positioned on a point that is within the left lateral one third of the length of the frame, measured hinge to hinge. The second retention mechanism may be positioned on a point that is within the right lateral one third of the frame. A third retention mechanism may also be used, located within the central one third of the frame, preferably at or near the midline. Four or five or more retention mechanisms may also be used, depending upon the desired performance. Typically, the retention mechanisms can be symmetrically spaced apart along the length of the frame, or as a mirror image across the plane of symmetry (anatomical midline).

In some embodiments that comprise dual lenses, each lens can be engaged and/or supported by at least one retention component. The retention mechanisms can include any of the passive or active retention mechanisms disclosed herein. For example, a dual lens may be secured to and/or supported by the frame using a first retention mechanism on the left side of a midline and a second retention mechanism on the right side of the midline. In some embodiments, a dual lens can be secured by three or more retention components, for example, at both lateral sides and a central portion thereof. A dual lens may be secured by a single retention component and by engagement between the dual lens and the frame, such as with a protrusion, catch, or tab that engages a recess of the frame. As with the unitary lens embodiments discussed above, typically, the retention mechanisms can be symmetrically spaced apart along the length of the frame, or as a mirror image across the plane of symmetry (anatomical midline).

Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions.

What is claimed is:

1. Eyewear comprising:
   a frame configured to support at, least one lens in a field of view of a wearer, the frame being configured to be worn on the wearer's head, the frame comprising a latch device; and
   at least one lens having a first engagement portion being configured to engage with the latch device for preventing the lens from separating from the frame;
   wherein the latch device comprises:
      an engagement structure that is movable relative to the lens along a path in a direction toward the first engagement portion of the lens, the engagement structure movable between a disengaged position and an engaged position for engaging with the first engagement portion of the lens to restrain movement of the lens, the engagement structure disposed on a slider arm; and
      a crank arm that is rotatably coupled relative to the frame and to the slider arm to form a slider-crank assembly, the slider-crank assembly allowing rotation of the crank arm to provide movement of the engagement structure.

2. The eyewear of claim 1, wherein the at least one lens further comprises a lens catch, and the frame further comprises a second engagement portion, the second engagement portion being configured to engage with the lens catch.

3. The eyewear of claim 2, wherein the second engagement portion of the lens comprises a recess in a body of the lens, and wherein the lens catch comprises a protrusion extending from the frame, the recess of the lens being configured to engage with the protrusion.

4. The eyewear of claim 1, wherein the first engagement portion of the lens comprises an elongate aperture extending through the lens.

5. The eyewear of claim 4, wherein the engagement structure of the latch device comprises a protrusion, the protrusion being movable into the elongate aperture of the lens for securing the lens relative to the frame.

6. The eyewear of claim 5, wherein the protrusion extends from the slider arm, the slider being rotatable and movable for moving the protrusion of the engagement structure within the aperture of the lens.

7. The eyewear of claim 6, wherein the latch device comprises an elongate slot formed in the frame, the protrusion of the engagement structure being disposed through and movable within the slot of the frame for facilitating movement between the engaged and disengaged positions.

8. The eyewear of claim 6, wherein the frame comprises a groove configured to receive the first engagement portion of the lens, the protrusion of the engagement structure of the latch device being passable into the groove of the frame for engaging the aperture of the lens upon movement from the disengaged position to the engaged position.

9. The eyewear of claim 1, wherein the path of the engagement structure intersects with the lens at an acute angle.

10. The eyewear of claim 1, wherein the frame is an eyeglass frame comprising a first ear stem and a second ear stem.

11. The eyewear of claim 1, wherein the first engagement portion of the lens comprises an elongate through-hole extending through the lens.

12. An eyeglass frame comprising:
a first ear stem and a second ear stem, the frame being configured to be worn on the wearer's head;
the frame defining first and second retention sections positioned intermediate the first and second earstems on the frame for supporting a lens in the field of view of a wearer; and
a lens retention system comprising a lens catch and a latch device, the lens catch being disposed in the first retention section of the frame, the latch device being disposed in the second retention section of the frame, the latch device comprising an engagement structure that is movable relative to the lens along a path in a direction toward a lens fitted against the frame, the engagement structure movable between a disengaged position and an engaged position for securing the lens relative to the frame;
wherein the latch device comprises a crank arm that is rotatably coupled relative to the frame and to a slider arm to form a slider-crank assembly, the slider arm comprising the engagement structure, the slider-crank assembly configured such that downward rotation of the slider arm causes movement of the engagement structure along the path from the engaged position to the disengaged position.

13. The frame of claim 12, wherein the path of the engagement structure is oriented at an acute angle relative to the lens.

14. The frame of claim 12, wherein the frame comprises first and second lens supports for supporting a pair of lenses, each lens support comprising a groove and lens retention means for securing the lens relative to the frame.

15. The frame of claim 12, wherein the frame comprises an elongate slot formed in the second retention section thereof, the slot being configured to receive the engagement structure of the latch device such that the engagement structure moves within the slot for moving between the engaged and disengaged positions for securing a lens relative to the frame.

16. An eyeglass comprising:
at least one lens having an engagement portion; and
a frame configured to support the lens in a field of view of a wearer, the frame comprising a latch device for securing the lens relative to the frame, the latch device comprising a crank arm, a slider arm, and an engagement structure disposed on the slider arm, the crank arm being rotatably connected relative to the frame and to the slider arm, the engagement structure being movable between a disengaged position and an engaged position for engaging with the engagement portion of the lens and restraining movement of the lens, the engagement structure defining a travel path that intersects with the engagement portion of the at least one lens at an acute angle.

17. The eyeglass of claim 16, wherein the frame comprises an elongate slot, the elongate slot being disposed adjacent to the latch device, the engagement structure comprising a protrusion that extends from the slider arm into the elongate slot of the frame for facilitating generally linear movement of the engagement structure relative to the frame.

18. The eyeglass of claim 17, wherein the engagement portion of the lens comprises an aperture and in the engaged position the protrusion of the engagement structure extends through the elongate slot into the aperture of the lens to engage the lens.

19. The eyeglass of claim 16, wherein the frame comprises a lens catch and the lens comprises first and second engagement portions, the first engagement portion of the lens being configured to engage with the lens catch of the frame, the second engagement portion being configured to engage with the latch device for preventing the lens from separating relative to the frame.

20. The eyeglass of claim 19, wherein the first engagement portion of the lens comprises a recess in a body of the lens and the lens catch comprises a protrusion configured to engage with the recess of the lens.

21. The eyeglass of claim 16, wherein the engagement portion of the lens comprises an elongate through-hole extending through the lens.

* * * * *

UNITED STATES PATENT AND TRADEMARK OFFICE
CERTIFICATE OF CORRECTION

| | | |
|---|---|---|
| PATENT NO. | : 8,668,330 B2 | Page 1 of 1 |
| APPLICATION NO. | : 13/209039 | |
| DATED | : March 11, 2014 | |
| INVENTOR(S) | : Reyes et al. | |

It is certified that error appears in the above-identified patent and that said Letters Patent is hereby corrected as shown below:

Title Page (item 75, Inventors) at lines 4-5, Change "Hanz" to --Hans--.

Signed and Sealed this
Sixteenth Day of September, 2014

Michelle K. Lee
*Deputy Director of the United States Patent and Trademark Office*